(12) United States Patent
Villareal

(10) Patent No.: US 7,485,335 B2
(45) Date of Patent: *Feb. 3, 2009

(54) STENT MOUNTING DEVICE AND A METHOD OF USING THE SAME TO COAT A STENT

(75) Inventor: Plaridel K. Villareal, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 499 days.

This patent is subject to a terminal disclaimer.

(21) Appl. No.: 10/997,478

(22) Filed: Nov. 24, 2004

(65) Prior Publication Data

US 2005/0096730 A1    May 5, 2005

Related U.S. Application Data

(60) Continuation of application No. 10/421,523, filed on Apr. 22, 2003, now Pat. No. 6,887,510, which is a division of application No. 09/873,020, filed on May 31, 2001, now Pat. No. 6,605,154.

(51) Int. Cl.
    *B05D 3/12* (2006.01)
(52) U.S. Cl. ..................................... 427/2.25
(58) Field of Classification Search ................ 606/191, 606/198; 623/1.11, 1.12; 427/2.3, 2.25, 427/2.28, 2.4; 29/508, 715, 407.08
See application file for complete search history.

(56) References Cited

U.S. PATENT DOCUMENTS

| | | | |
|---|---|---|---|
| 4,629,563 A | 12/1986 | Wrasidlo | |
| 4,733,665 A | 3/1988 | Palmaz | |
| 4,800,882 A | 1/1989 | Gianturco | |
| 4,886,062 A | 12/1989 | Wiktor | |
| 4,906,423 A | 3/1990 | Frisch | |
| 5,037,427 A | 8/1991 | Harada et al. | |
| 5,171,445 A | 12/1992 | Zepf | |
| 5,188,734 A | 2/1993 | Zepf | |
| 5,229,045 A | 7/1993 | Soldani | |
| 5,234,457 A | 8/1993 | Andersen | |
| 5,537,729 A | 7/1996 | Kolobow | |
| 5,611,775 A | 3/1997 | Machold et al. | |
| 5,624,411 A | 4/1997 | Tuch | |
| 5,628,786 A | 5/1997 | Banas et al. | |
| 5,772,864 A | 6/1998 | Møller et al. | |
| 5,788,626 A | 8/1998 | Thompson | |
| 5,820,917 A | 10/1998 | Tuch | |
| 5,823,996 A | 10/1998 | Sparks | |
| 5,833,659 A | 11/1998 | Kranys | |
| 5,855,598 A | 1/1999 | Pinchuk | |
| 5,865,814 A | 2/1999 | Tuch | |
| 5,895,407 A | 4/1999 | Jayaraman | |
| 5,897,911 A * | 4/1999 | Loeffler | 427/2.25 |
| 5,922,393 A | 7/1999 | Jayaraman | |
| 5,935,135 A | 8/1999 | Bramfitt et al. | |
| 5,948,018 A | 9/1999 | Dereume et al. | |
| 6,010,573 A | 1/2000 | Bowlin | |
| 6,045,899 A | 4/2000 | Wang et al. | |
| 6,056,993 A | 5/2000 | Leidner et al. | |

(Continued)

*Primary Examiner*—Kevin T Truong
(74) *Attorney, Agent, or Firm*—Squire Sanders & Dempsey LLP

(57) ABSTRACT

A stent mounting device and a method of coating a stent using the device are provided.

24 Claims, 3 Drawing Sheets

U.S. PATENT DOCUMENTS

| | | |
|---|---|---|
| 6,059,714 A | 5/2000 | Armini et al. |
| 6,120,847 A | 9/2000 | Yang et al. |
| 6,126,686 A | 10/2000 | Badylak et al. |
| 6,153,252 A | 11/2000 | Hossainy et al. |
| 6,156,373 A | 12/2000 | Zhong et al. |
| 6,214,115 B1 | 4/2001 | Taylor et al. |
| 6,245,099 B1 | 6/2001 | Edwin et al. |
| 6,258,121 B1 | 7/2001 | Yang et al. |
| 6,279,368 B1 | 8/2001 | Escano et al. |
| 6,322,586 B1 * | 11/2001 | Monroe et al. ............. 623/1.11 |
| 6,322,847 B1 | 11/2001 | Zhong et al. |
| 6,364,903 B2 | 4/2002 | Tseng et al. |
| 6,387,118 B1 | 5/2002 | Hanson |
| 6,521,284 B1 | 2/2003 | Parsons et al. |
| 6,527,863 B1 | 3/2003 | Pacetti et al. |
| 6,565,659 B1 | 5/2003 | Pacetti et al. |

* cited by examiner

STENT MOUNTING DEVICE AND A METHOD OF USING THE SAME TO COAT A STENT

CROSS REFERENCE

This is a continuation application of U.S. Ser. No. 10/421,523, filed on Apr. 22, 2003 now U.S. Pat. No. 6,887,510, which is a divisional application of U.S. Ser. No. 09/873,020, now U.S. Pat. No. 6,605,154, filed on May 31, 2001.

BACKGROUND OF THE INVENTION

1. Field of the Invention

This invention relates to a stent mounting device and a method of coating a stent using the device.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of rigid but resiliently flexible struts 12 that are arranged in a sinusoidal-like configuration to form a continuous ring or cylinder. The plurality of struts 12 are radially expandable, disposed coaxially, and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus with which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating on or between the stent struts. Upon the removal of the coated stent from the supporting apparatus, the excess coating may stick to the apparatus, thereby removing some of the needed coating from the stent and leaving bare areas. Alternatively, the excess coating may stick to the stent, thereby leaving excess coating as clumps or pools on the struts or webbing between the struts.

Thus, it is desirable to minimize the interface between the stent and the apparatus supporting the stent during the coating process to minimize coating defects. Accordingly, the present invention provides for a device for supporting a stent during the coating application process. The invention also provides for a method of coating the stent supported by the device.

SUMMARY OF THE INVENTION

The present invention provides an apparatus for supporting a hollow, cylindrical stent. The apparatus includes a mounting assembly for releasably holding a stent in a fixed position without being in contact with a majority of the area of the inner surface of the stent. The mounting assembly can be used for supporting a stent during the process of forming a coating on the stent.

In one embodiment, the mounting assembly includes a first coning end that can be inserted within a first end of the stent and a second coning end that can be inserted within an opposing second end of the stent. The coning ends are used for securely pinching the stent.

In one embodiment, the mounting assembly includes a first member for making contact with a first end of the stent, a second member for making contact with a second end of the stent, and a third member for extending within the hollow, cylindrical stent and for securing the first member to the second member. The distance between the first member and the second member can be adjusted by inserting the third member deeper into the first member or the second member.

The mounting assembly can apply a force on a first end of the stent in a first direction and an opposite force on a second end of the stent in a second direction. Accordingly, the mounting assembly prevents any significant movement of the stent.

In one embodiment, the means for applying the forces to the first and second ends of the stent are defined by a pair of members having inwardly tapered ends that penetrate at least partially in the first and second ends of the stent and are in contact with an inner rim of the first and second ends of the stent. In another embodiment, one of the inwardly tapered ends can be incrementally moved closer to the other inwardly tapered end so as to increase the forces applied to the first and second ends of the stent.

The present invention also provides a method of coating a stent. The method includes mounting a stent on a support assembly and forming a coating on the stent. The support assembly does not contact a significant portion of the inner surface of the stent. In one embodiment, the act of mounting includes positioning one end of the stent over a coned end of a first member, positioning a coned end of a second member within the opposing end of the stent, and reducing the distance between the coned ends such that the stent is securely pinched between the coned ends.

In one embodiment, the stent can be at least partially expanded prior to mounting the stent on the support assembly. The coating can be applied by spraying a composition at the stent. Translational and/or rotational motion can be provided during the coating process.

DETAILED DESCRIPTION

Embodiments of the Mounting Assembly

Figure 1:
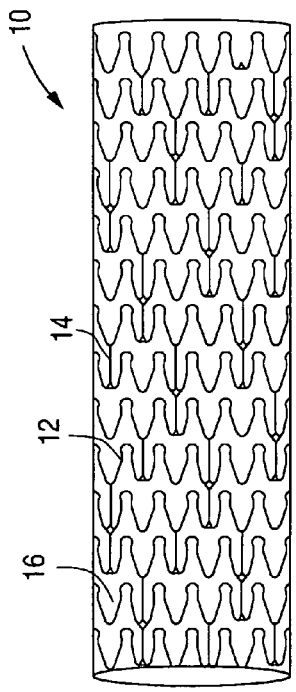
FIG. 1 illustrates a conventional stent.
Figure 2A:
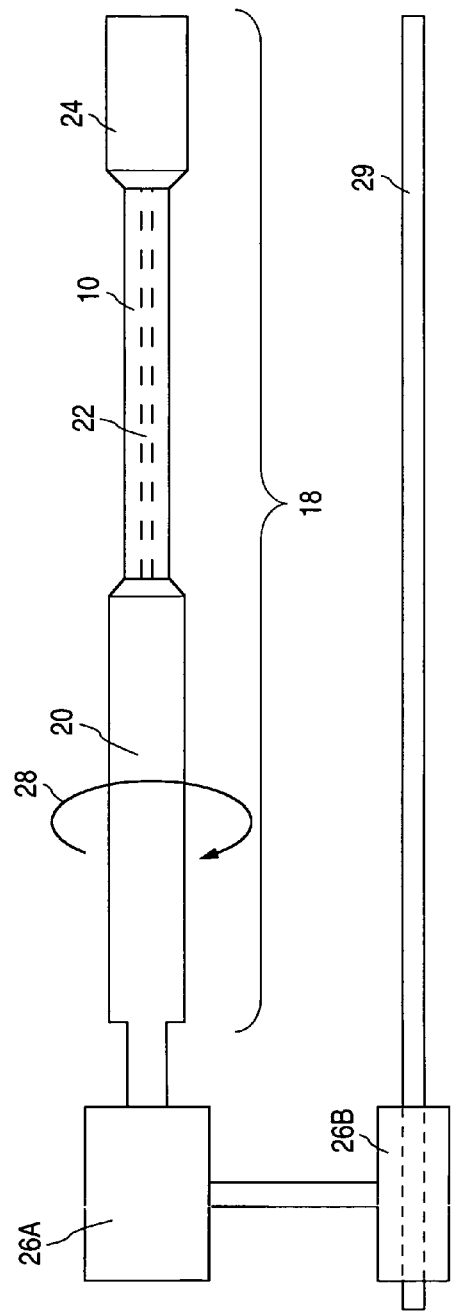
FIG. 2A illustrates a mounting assembly for supporting a stent in accordance with one embodiment of the present invention.

Referring to FIG. 2A, a mounting assembly 18 for supporting stent 10 is illustrated to include a support member 20, a mandrel 22, and a lock member 24. Support member 20 can connect to a motor 26A so as to provide rotational motion about the longitudinal axis of stent 10, as depicted by arrow 28, during the coating process. Another motor 26B can also be provided for moving support member 20 in a linear direction, back and forth, along a rail 29.

Figure 2B:
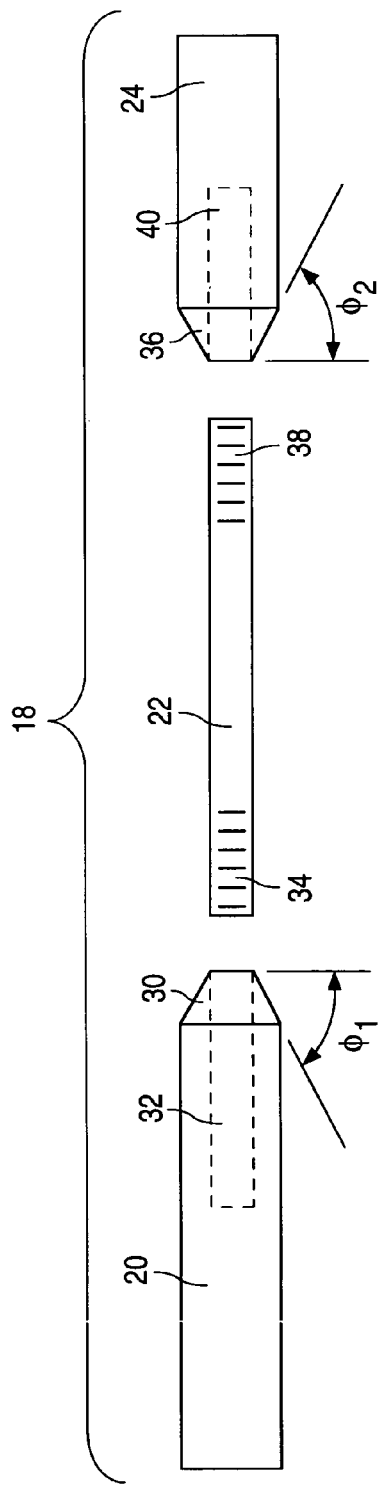
FIG. 2B illustrates an expanded view of the mounting assembly in accordance with one embodiment of the present invention.

Referring to FIG. 2B, support member 20 includes a coning end portion 30, tapering inwardly at an angle $\Phi_1$ of about 15° to about 75°, more narrowly from about 30° to about 60°. By way of example, angle $\Phi_1$ can be about 45°. In accordance with one embodiment, mandrel 22 can be permanently affixed to coning end portion 30. Alternatively, support member 20 can include a bore 32 for receiving a first end 34 of mandrel 22. First end 34 of mandrel 22 can be threaded to screw into bore 32. Bore 32 should be deep enough so as to allow mandrel 22 to securely mate with support member 20. The depth of bore 32 can also be over-extended so as to allow a significant length of mandrel 22 to penetrate or screw into bore 32. This would allow the length of mandrel 22 to be adjusted to accommodate stents of various sizes.

The outer diameter of mandrel 22 can be smaller than the inner diameter of stent 10 so as to prevent the outer surface of mandrel 22 from making contact with the inner surface of stent 10. A sufficient clearance between the outer surface of mandrel 22 and the inner surface of stent 10 should be provided to prevent mandrel 22 from obstructing the pattern of the stent body during the coating process. By way of example, the outer diameter of mandrel 22 can be from about 0.010 inches (0.254 mm) to about 0.012 inches (0.305 mm) when the stent has an inner diameter of between about 0.025 inches (0.635 mm) and about 0.035 inches (0.889 mm).

Lock member 24 includes a coning end portion 36 having an inwardly tapered angle $\Phi_2$. Angle $\Phi_2$ can be the same as or different than the above-described angle $\Phi_1$. A second end 38 of mandrel 22 can be permanently affixed to lock member 24 if end 34 is disengagable from support member 20. Alternatively, in accordance with another embodiment, mandrel 22 can have a threaded second end 38 for screwing into a bore 40 of lock member 24. Bore 40 can be of any suitable depth that would allow lock member 24 to be incrementally moved closer to support member 20. Accordingly, stents 10 of any length can be securely pinched between support and lock members 20 and 24. In accordance with yet another embodiment, a non-threaded second end 38 and bore 40 combination is employed such that second end 38 can be press-fitted or friction-fitted within bore 40 to prevent movement of stent 10 on mounting assembly 18.

Figure 3:
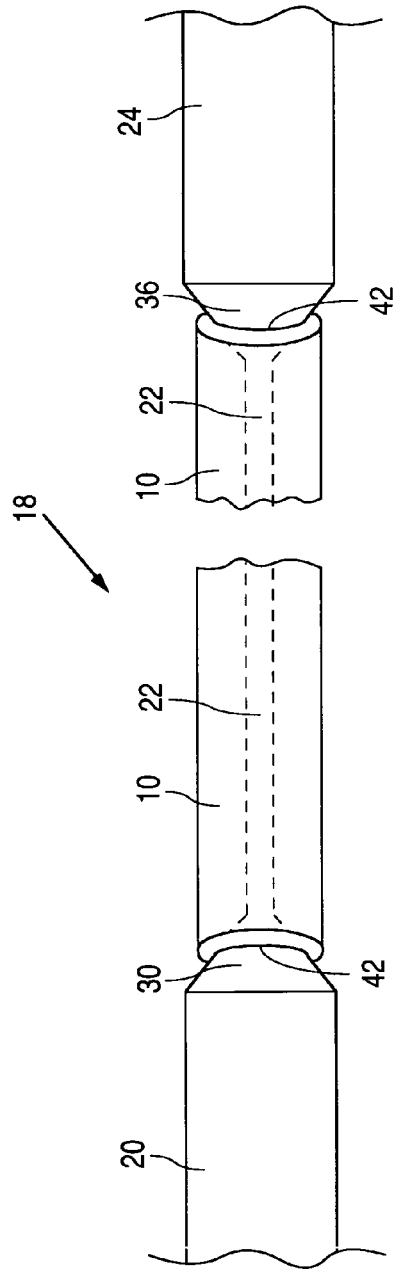
FIG. 3 illustrates the interface between the mounting assembly and the stent.

Mounting assembly 18 supports stent 10 via coning end portions 30 and 36. FIG. 3 illustrates the interface between coning end portions 30 and 36 and an inner rim 42 at each end of stent 10 so as to provide minimal contact between stent 10 and mounting assembly 18. Opposing forces exerted from support and lock members 20 and 24, for securely pinching stent 10, should be sufficiently strong so as to prevent any significant movement of stent 10 on mounting assembly 18. However, the exerted force should not compress stent 10 so as to distort the body of stent 10. Over or under application of support force can lead to coating defects, such as non-uniformity of the coating thickness.

Coating a Stent Using the Mounting Assembly

The following method of application is being provided by way of illustration and is not intended to limit the embodiments of mounting assembly 18 of the present invention. A spray apparatus, such as EFD 780S spray device with VALVEMATE 7040 control system (manufactured by EFD Inc., East Providence, R.I.), can be used to apply a composition to a stent. EFD 780S spray device is an air-assisted external mixing atomizer. The composition is atomized into small droplets by air and uniformly applied to the stent surfaces. The atomization pressure can be maintained at a range of about 5 psi to about 20 psi. The droplet size depends on such factors as viscosity of the solution, surface tension of the solvent, and atomization pressure. Other types of spray applicators, including air-assisted internal mixing atomizers and ultrasonic applicators, can also be used for the application of the composition.

During the application of the composition, a stent supported by mounting assembly 18 can be rotated about the stent's central longitudinal axis. Rotation of the stent can be from about 1 rpm to about 300 rpm, more narrowly from about 50 rpm to about 150 rpm. By way of example,. the stent can rotate at about 120 rpm. The stent can also be moved in a linear direction along the same axis. The stent can be moved at about 1 mm/second to about 12 mm/second, for example about 6 mm/second, or for a minimum of at least two passes (i.e., back and forth past the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition can be, for example, about 1 second to about 10 seconds in duration. The amount of coating applied by each repetition can be about 0.1 micrograms/cm (of stent surface) to about 10 micrograms/cm, for example less than about 2 micrograms/cm per 5-second spray.

Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2-4 hours) or by the application of warm air. The application of warm air between each repetition prevents coating defects and minimizes interaction between the active agent and the solvent. The temperature of the warm air can be from about 30° C. to about 60° C., more narrowly from about 40° C. to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds. Any suitable number of repetitions of applying the composition followed by removing the solvent(s) can be performed to form a coating of a desired thickness or weight. Excessive application of the polymer can, however, cause coating defects.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

In accordance with one embodiment, the stent can be at least partially pre-expanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent for increasing the interspace between the stent struts during the application of the composition, can further prevent "cob web" or "pool web" formation between the stent struts.

In accordance with one embodiment, the composition can include a solvent and a polymer dissolved in the solvent and optionally a wetting fluid. The composition can also include active agents, radiopaque elements, or radioactive isotopes. Representative examples of polymers that can be used to coat a stent include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly (amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The active agent can be any substance capable of exerting a therapeutic or prophylactic effect in a patient. Examples of such agents include antiproliferative, antineoplastic, antiinflammatory, antiplatelet, anticoagulant, antifibrin, antithrombin, antimitotic, antibiotic, and antioxidant substances as well as combinations thereof. A suitable example of an antiproliferative substance is actinomycin D, or derivatives and analogs thereof. Synonyms of actinomycin D include dactinomycin, actinomycin IV, actinomycin $I_1$, actinomycin $X_1$, and actinomycin $C_1$. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mitamycin. Examples of suitable cytostatic or antiproliferative agents include angiopeptin (a somatostatin analog from Ibsen), angiotensin converting enzyme inhibitors such as captopril (available from Squibb), cilazapril (available from Hoffman-LaRoche), or lisinopril (available from Merck); calcium channel blockers (such as nifedipine), colchicine, fibroblast growth factor (FGF) antagonists, fish oil (omega 3-fatty acid), histamine antagonist, lovastatin (an inhibitor of HMG-CoA reductase, a cholesterol lowering drug from Merck), monoclonal antibodies (such as PDGF receptors), nitroprusside, phosphodiesterase inhibitors, prostaglandin inhibitor (available from Glaxo), suramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, rapamycin, and dexamethasone. Exposure of the active ingredient to the composition should not adversely alter the active ingredient's composition or characteristic. Accordingly, the particular active ingredient is selected for compatibility with the solvent or blended polymer-solvent.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

EXAMPLE

Figure 4A:
FIG. 4A illustrates uncoated stent struts as described in the Example.
Figure 4B:
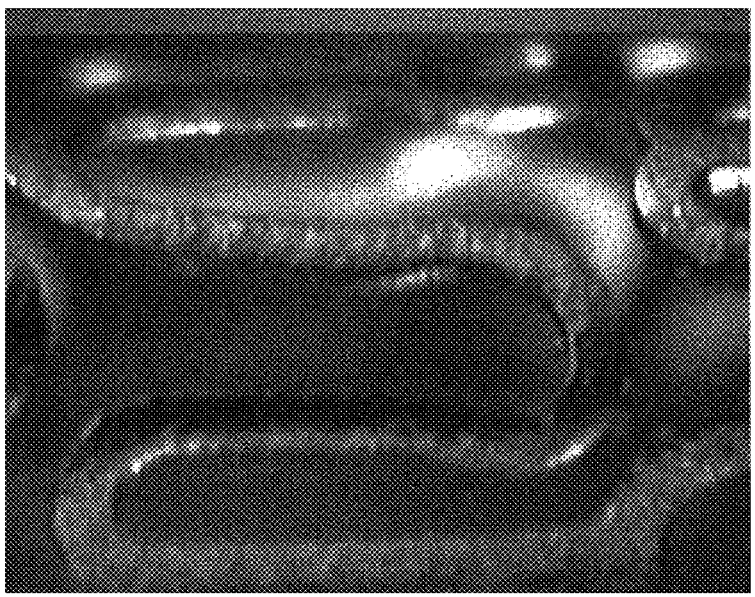
FIG. 4B illustrates stent struts coated in accordance with the procedure described in the Example.

FIG. 4A illustrates uncoated struts of a Multi-Link SOLO stent (available from Guidant Corporation). By contrast, FIG. 4B illustrates struts of a Multi-Link SOLO stent that was spray-coated to yield a uniform coating on the surfaces of the stent struts in accordance with the protocol set forth below.

Eighteen 3.0 mm Multi-Link SOLO stents were spray-coated while supported by mounting assembly 18 of the present invention. The stents had been previously passivated to remove surface contaminants, such as exogenous iron compounds, by chemically treating the stents, for example with an acid solution.

A 0.1% heparin solution was prepared by dissolving 0.5 g of Duraflo II heparin powder (a heparin derivative offered by Baxter International) with 500 ml of Genesolv 2004 solvent (obtained from Allied Signal, Ontario, Canada). A 0.5% heparin solution was prepared by dissolving 2.5 g of Duraflo II heparin powder with 500 ml of Genesolv 2004 solvent.

Support member 20 was inserted into a rotatable collet, and the connection was tested by rotating the collet to ensure that support member 20 moved steadily as the collet turned. A stent was positioned on mandrel 22 attached to support member 20, and lock member 24 was then threaded onto mandrel 22. The mounted stent was inspected to ensure that the stent was sitting straight on mounting assembly 18 and that the inner rim at each end of the stent was positioned firmly on coning end portions 30 and 36 of the support and lock members 20 and 24.

A Vega 2000 Air Brush (obtained from Dixie Art Supplies, New Orleans, La.) was used to apply the compositions to the stents. The spray nozzle was adjusted to provide a distance from the nozzle tip to the outer surface of the stent of 1.5±0.25 inches (3.81±0.64 cm) and a spray angle of 90°±3° relative to the horizontal stents. The atomization pressure was set to be maintained throughout the coating process at 10±2 psi.

The stents were coated using varied parameters. Ten stents were spray-coated with the 0.1% heparin solution, and eight stents were spray-coated with the 0.5% heparin solution. The insides of the spray nozzle and related tubing were cleaned by purging with Genesolv 2004, both initially and upon each change of solution. Ten of the stents were rotated about the stent's central longitudinal axis at a speed of 90±5 rpm during coating, while eight of the stents were rotated at a speed of 110±5 rpm during coating. Two of the stents were coated by a stationary nozzle, while sixteen of the stents were coated by a nozzle that traversed along the length of the stent at a speed of about 0.875 inch (2.22 cm) per second. Ten of the stents were coated using an injection rate of 163.6 ml per hour, and eight of the stents were coated using an injection rate of 200 ml per hour. Nine of the stents were coated with a total volume of 2.5 ml of solution, while nine of the stents were coated with a total volume of 5 ml of solution.

The solvent in the heparin solutions had evaporated essentially upon contact with the stents to form a coating thereon. Each coated stent was removed from mounting assembly 18 and placed in a clear vial. While in the clear vial, each stent was visually inspected under a microscope at 150× magnification. A rating scheme of 0-2 was established to determine the acceptability of the coated stents. A rating of 0 indicated the presence of flakes, peeling, or webbing, excess coating on some portions of the stent, and/or blank spaces on the stent. A rating of 1 indicated that the stent was coated on the inside and outside surfaces without blank spaces but may have excess coating in some areas. A rating of 2 indicated that the stent was coated on the inside and outside surfaces without defects such as flakes, peeling, webbing, blank spaces, or excess coating on some portions of the stent. The results of the study, as tabulated below, indicated that mounting assembly 18 of the present invention provides for the uniform coating of the inner and outer surfaces of stents.

| Run | Heparin Conc. (%) | Injection. Rate (ml/hr) | Total Volume (ml) | Rotation speed (rpm) | Nozzle Traverse (Yes or No) | Visual Inspection. Rating (0, 1, or 2) |
|---|---|---|---|---|---|---|
| 1 | 0.1 | 200.0 | 2.5 | 90 | Yes | 2 |
| 2 | 0.1 | 163.6 | 5.0 | 90 | Yes | 2 |
| 3 | 0.1 | 163.6 | 5.0 | 110 | Yes | 2 |
| 4 | 0.1 | 200.0 | 2.5 | 110 | Yes | 1 |
| 5 | 0.1 | 200.0 | 5.0 | 90 | Yes | 1 |
| 6 | 0.1 | 163.6 | 2.5 | 110 | Yes | 1 |
| 7 | 0.1 | 163.6 | 2.5 | 90 | Yes | 1 |
| 8 | 0.1 | 200.0 | 5.0 | 110 | Yes | 2 |
| 9 | 0.5 | 163.6 | 5.0 | 110 | Yes | 2 |
| 10 | 0.5 | 200.0 | 5.0 | 110 | Yes | 1 |
| 11 | 0.5 | 163.6 | 2.5 | 90 | Yes | 2 |
| 12 | 0.5 | 200.0 | 5.0 | 90 | Yes | 1 |
| 13 | 0.5 | 200.0 | 2.5 | 110 | Yes | 1 |
| 14 | 0.5 | 200.0 | 2.5 | 90 | Yes | 2 |
| 15 | 0.5 | 163.6 | 2.5 | 110 | Yes | 1 |
| 16 | 0.5 | 163.6 | 5.0 | 90 | Yes | 1 |
| 17 | 0.1 | 163.6 | 2.5 | 90 | No | 1 |
| 18 | 0.1 | 200.0 | 5.0 | 90 | No | 1 |

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An apparatus for supporting a stent so as to allow a coating composition to be applied to the stent, comprising:
   a first structural element to make contact with a first position of a stent;
   a second structural element to make contact with a second position of the stent; and
   an incremental adjusting element to allow the first structural element to be moved incrementally closer to the second structural element so as to apply a force on the stent to hold the stent in a supporting position;
   wherein the stent is releasably held in a position without having the apparatus in contact with a majority of an outer surface of the stent so as to allow a coating composition to be applied to at least the outer surface of the stent.

2. The apparatus of claim 1, wherein the adjusting element allows for the application of a controlled force on the stent so as to minimize or prevent damage to a coating deposited on the stent.

3. The apparatus of claim 1, wherein the adjusting element includes a third structural element which incrementally couples the first structural element to the second structural element.

4. The apparatus of claim 3, wherein the third structural element is threaded at each end, and one end screws into a bore in the first structural element and the other end screws into a bore in the second structural element.

5. The apparatus of claim 1, wherein the adjusting element includes a third structural element which incrementally couples the first structural element to the second structural element and is adapted to be extended through a hollow bore of the stent.

6. The apparatus of claim 5, wherein the third structural element is threaded at each end, and one end screws into a bore in the first structural element and the other end screws into a bore in the second structural element.

7. The apparatus of claim 1, wherein the first structural element is configured to at least partially penetrate into one open end of the stent.

8. The apparatus of claim 7, wherein the second structural element is configured to at least partially penetrate into an opposing end of the stent.

9. The apparatus of claim 1, wherein at least one of the structural elements includes a conical shaped portion to allow the smaller end of the conical shaped portion to penetrate into one end of the stent.

10. The apparatus of claim 9, additionally including a third structural element coupling the first structural element to the second structural element.

11. The apparatus of claim 10, wherein the third structural element is threaded at each end, and one end screws into a bore in the first structural element and the other end screws into a bore in the second structural element.

12. The apparatus of claim 10, wherein the third structural element extends though a longitudinal bore of the stent.

13. The apparatus of claim 12, wherein the third structural element does not contact an inner surface of the stent.

14. The apparatus of claim 9, additionally including a third structural element coupled to the first and/or second structural elements and configured to be extended through a hollow bore of the stent.

15. The apparatus of claim 1, additionally including a third structural element coupling the first structural element to the second structural element by extending through a longitudinal bore of the stent.

16. The apparatus of claim 15, wherein the third structural element does not contact an inner surface of the stent.

17. The apparatus of claim 1, additionally including a third structural element coupling the first structural element to the second structural element, wherein the first structural element only contacts one end of the stent and the second structural element only contacts an opposing end of the stent.

18. The apparatus of claim 17, wherein the third structural element extends through the longitudinal bore of the stent.

19. The apparatus of claim 18, wherein the third structural element does not contact an inner surface of the stent.

20. An apparatus for supporting a stent so as to allow a coating composition to be applied to the stent, comprising:
  a first structural element to make contact with a first position of a stent;
  a second structural element to make contact with a second position of the stent; and
  means for allowing the structural elements to be moved incrementally closer to one another for incrementally adjusting the distance between the first and second structural elements so as to apply a force on the stent to hold the stent in a supporting position;
  wherein the stent is releasably held in a position without having the apparatus in contact with a majority of an outer surface of the stent so as to allow a coating composition to be applied to at least the outer surface of the stent.

21. The apparatus of claim 20, wherein means for allowing the structural elements to be moved incrementally closer to one another allows for the application of a controlled force on the stent so as to minimize or prevent damage to a coating deposited on the stent.

22. The apparatus of claim 20, additionally including a third structural element coupling the first structural element to the second structural element, wherein the first structural element only contacts one end of the stent and the second structural element only contacts an opposing end of the stent.

23. The apparatus of claim 22 wherein the third structural element extends through the longitudinal bore of the stent.

24. The apparatus of claim 23, wherein the third structural element does not contact an inner surface of the stent.

* * * * *